United States Patent [19]

Obzansky et al.

[11] Patent Number: 5,324,650
[45] Date of Patent: Jun. 28, 1994

[54] SITU PROCESS FOR PRODUCTION OF CONJUGATES

[75] Inventors: David M. Obzansky, Elkton, Md.; Susan Y. Tseng, Hockessin, Del.

[73] Assignee: E. I. Du Pont de Nemours and Company, Wilmington, Del.

[21] Appl. No.: 946,247

[22] Filed: Sep. 17, 1992

Related U.S. Application Data

[63] Continuation of Ser. No. 495,576, Mar. 20, 1990, abandoned.

[51] Int. Cl.[5] ............ C12N 9/96; G01N 33/53; A61K 39/42; A61K 37/62
[52] U.S. Cl. .................. 435/188; 435/7.1; 435/7.6; 435/964; 424/85.8; 424/94.3
[58] Field of Search ............ 424/85.8, 94.3; 435/7.1, 7.6, 188, 964

[56] References Cited

U.S. PATENT DOCUMENTS 4,231,999 11/1980 Carlsson et al. ............ 435/7.8
4,232,119 11/1980 Carlsson et al. ............ 530/391.5
4,810,638 3/1989 Albarella et al. ............ 435/188
4,843,001 6/1989 Haug et al. ............ 435/7.9

FOREIGN PATENT DOCUMENTS 210863 2/1987 European Pat. Off. .

OTHER PUBLICATIONS

Hashida et al., Journal of Applied Biochemistry 6, 56–63 (1984).
Ishikawa et al., Clin. Biochem. 20: 375–385 (1987).
Gould (1959) "Mechanism and Structure in Organic Chemistry", pp. 258–259, Holt, Rinehart & Winston, Inc., New York.
Duncan et al. (1983) Anal. Biochem., 132, 68–73.
Pierce Immunology Catalog & Handbook (Jan. 1990) pp. E1→E16 see also A8–A11 (not enclosed).
Cattel et al., Cancer Immunol. Immunother. 27: 233–240 (1988).
Pack, Biochemistry, 27: 6633–6639 (1988).
Duncan et al. Analytical Biochemistry, 132: 68–73 (1983).
Derksen et al., Biochim. et Biophys. Acta 814: 151–155 (1985).
Peeters et al., J. Immunol. Methods, 120: 133–143 (1989).
Blumberg et al., Eur. J. Biochem., 136: 151–154 (1983).
Caruelle et al., Analytical Biochem., 173: 328–339 (1988).
CA 109: 196997s (1988).
CA 109: 110850d (Jan. 7, 1988).

Primary Examiner—Douglas W. Robinson
Assistant Examiner—Jon P. Weber

[57] ABSTRACT

In situ process for production of conjugates using a deblocking agent which allows conjugation to occur and two compositions wherein one composition is functionalized with a group capable of reacting efficiently with free thiols, and a second composition containing blocked thiols.

2 Claims, 11 Drawing Sheets

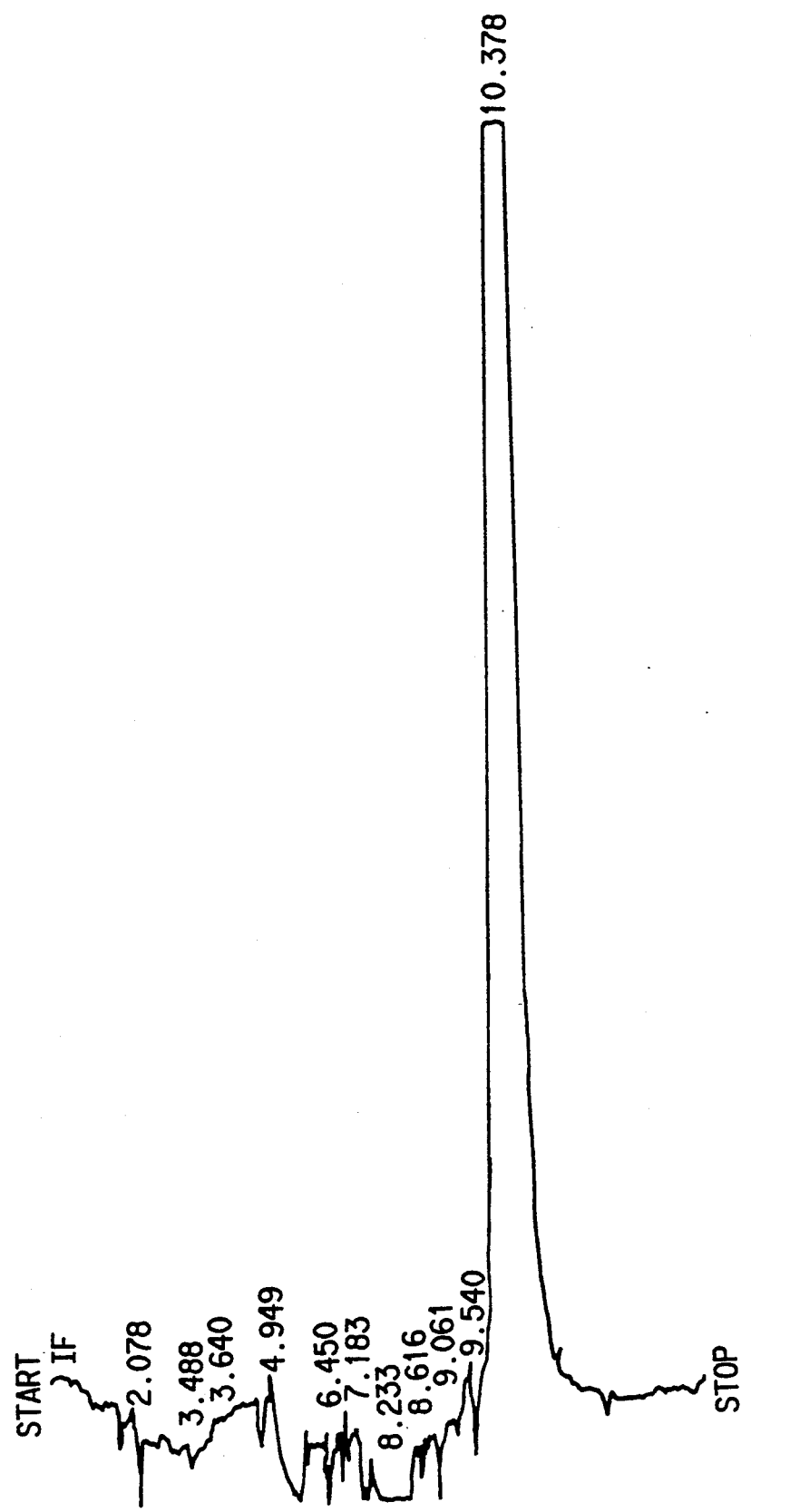

START
IF
9.099
9.723
12.905
STOP

START
IF
8.111
8.556
9.090
9.747
12.893
STOP

START
IF
8.111
8.560
9.090
9.746
12.395
STOP

SITU PROCESS FOR PRODUCTION OF CONJUGATES

This is a continuation of application Ser. No. 07/495,576 filed Mar. 20, 1990, now abandoned.

FIELD OF THE INVENTION

This invention relates to the production of conjugates and, in particular, to an in situ conjugation process.

BACKGROUND OF THE INVENTION

Antibody-based systems for diagnosis and therapy rest on development of chemistry for the covalent modification of antibodies, especially, monoclonal antibodies, as well as the further development of linker systems which can, for example, enhance the performance of drugs delivered by the antibody.

An important factor in the use of antibody-based systems concerns the quality and nature of the antibody conjugate used. Originally, aggregated antibody enzyme conjugates were produced using a nonspecific coupling chemistry such as glutaraldehyde crosslinking which was described by Avrameas, *Immunochemistry*, 6:43 (1969) or a periodate oxidation method as described by Boorsma et al., *Histochem. Cytochem.*, 23:200 (1974). The drawback with these approaches is that crosslinking is random and the antibodies are often buried deep within the resulting aggregated complex. Accordingly, the relative inaccessibility of antibodies reduces, if not eliminates altogether, their specific activity.

Recently, several approaches have been described in which both proteins, e.g., antibody and enzyme or toxin, are activated at their primary amine groups using an NHS-ester group of a heterobifunctional reagent to introduce a functional moiety such as a maleimide or sulfhydryl group. Imagawa et al., *J. Appl. Biochem.*, 4:400 (1982), Duncan et al., *Anal. Biochem.*, 132:68 (1983).

Three methods commonly used to thiolate involve introducing a free sulfhydryl group which is deblocked before proceeding with the conjugation. These methods include the following: (1) reaction with N-succinimidyl 3-(2-pyridyldithio)propionate (SPDP)as described by Carlsson et al., *Biochem. J.*, 173:723 (1978); or (2) reaction with 4-mercaptobutyrimidate in the presence of 4,4'-dithiodipyridine as described by King et al., *Immunol. Method*, 28:201 (1979); or reaction with S-acetyl mercaptosuccinic anhydride (SAMSA) as described by Weston et al., *Biochem. Biophys. Acta*, 612:40 (1980).

U.S. Pat. No. 4,231,999, issued to Carlsson et al. on Nov. 4, 1980, describes an assay method involving biospecific affinity reactions. Thiolation using SPDP involving subsequent reduction with dithiothreitol prior to conjugation.

U.S. Pat. No. 4,232,119, issued to Carlsson et al. on Nov. 4, 1980 describes reagents such as SPDP for use as reagents in immunoassays.

Duncan et al., *Analytical Biochemistry*, 132:68-73 (1983), descries the synthesis of the N-hydroxysuccinimide ester of S-acetylthioacetic acid (SATA) and its use in preparing conjugates.

Derksen et al., *Biochimica at Biophysica Acta*, 814:151-155 (1985), describe the use of SATA to couple proteins to liposomes containing maleimide residues.

Peeters et al., *J. Immunological Methods*, 120:133-143 (1989), describes a comparison of several coupling reagents such as SATA and SPDP on the antigenicity and immunogenicity of the conjugates.

The disadvantage of these approaches is that the thiolated protein tends to aggregate during the conjugation process. Protection of free sulfhydryl groups in solution from adventitious reaction, particularly oxidation, is almost impossible.

SUMMARY OF THE INVENTION

This invention relates to an in situ process for conjugating two compositions, wherein a first composition is functionalized with a group that can react efficiently with free thiols, is mixed simultaneously with a second composition containing blocked thiols, and a deblocking reagent which generates free thiol groups and permits conjugation of the two compositions to take place.

In another embodiment, the composition functionalized with a thiol reactive group can be mixed with a second composition having blocked thiol groups before adding the deblocking reagent.

Finally, the first composition functionalized with thiol reactive groups can be mixed with the deblocking reagent before adding the second composition having blocked thiol groups.

BRIEF DESCRIPTION OF THE DRAWINGS

FIG. 2B presents the chromatogram for acetyl-thiolated alkaline phosphatase.

FIG. 6A presents the chromatogram of anti-HCG-(Fab')$_2$ functionalized with a thiol reactive group and acetylthiolated streptavidin at T=0 minutes when $3 \times 10^{-5}$ mole/mL hydroxylamine deblocking reagent is added.

FIG. 6B presents the chromatogram of anti-HCG-(Fab')$_2$ functionalized with a thiol reactive group and acetylthiolated streptavidin at T=15 minutes when $3 \times 10^{-5}$ mole/mL hydroxylamine deblocking reagent is added.

FIG. 6C (like 6B except T=60 minutes).

DETAILED DESCRIPTION OF THE INVENTION

The process of the invention involves reacting simultaneously two compositions, one of which has a group capable of reacting efficiently with free thiols and one of which has blocked thiols with a deblocking reagent to generate free thiol groups, thus, permitting conjugation of the two compositions to occur. The composition functionalized with a thiol reactive group can be mixed with the second composition before adding the deblocking reagent. In still another embodiment, the composition functionalized with thiol reactive groups can be mixed with the deblocking reagent before adding the composition having blocked thiol groups. The resulting conjugates can then be utilized, for example, C in any automated clinical analyzer such as the aca ® discrete clinical analyzer which is manufactured by E. I. du Pont de Nemours and Company.

Figure 1A:
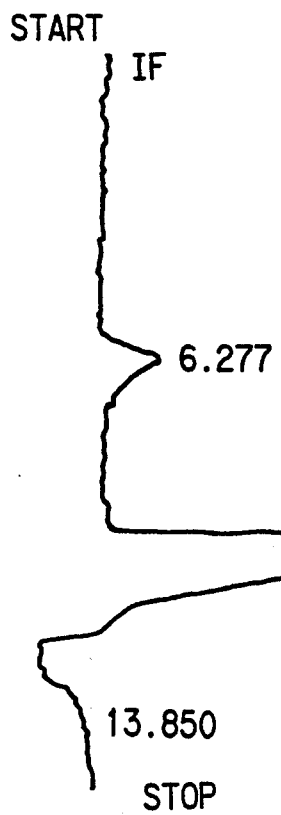
FIG. 1A presents the chromatogram for native anti-TSH-(Fab')$_2$ antibody fragments.
Figure 1B:
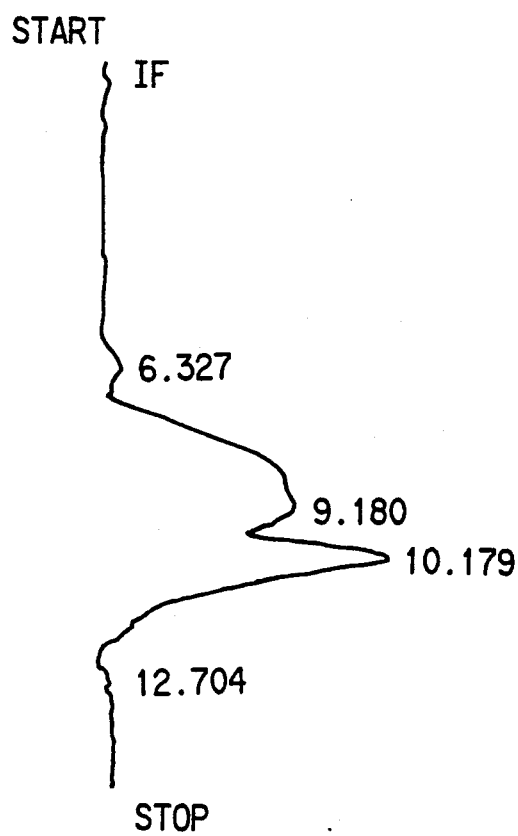
FIG. 1B presents the chromatogram for anti-TSH-(Fab')antibody fragments functionalized with a thiol reactive group.

Initiation of the reaction can be controlled while minimizing the formation of aggregates. The size of the resulting conjugate is controlled better than in the processes where the compositions are deblocked prior to conjugation. This undesirable aggregation problem is illustrated in FIG. 1 which shows aggregation of the antibody fragment, anti-TSH-(Fab')$_2$-SH which normally occurs after thiolation.

Advantages offered by the process of the invention include minimizing the formation of aggregates, allowing for superior control of the size of the conjugate, controlling conjugate production on different scales, obtaining a higher yield of conjugates having a higher specific activity.

Compositions which can be used in the process of the invention include proteins, peptides, nucleotides, modified lipid, or any particle or solid support with derivatized amine groups on the surface. Examples of modified lipids include liposomes modified to contain maleimide groups. Examples of particles include amino-silane coated chromium dioxide particles, and amino-silane coated phosphor particles, and any other solid surfaces or particles containing amine groups.

Any thiolation reagents which introduce blocked thiol groups can be used to practice the invention. Such reagents include succinimidyl S-acetylthioacetate (SATA), S-acetylmercaptosuccinic anhydride (SAMSA), and succinimidyl-3-(acetylthio)-propionate (SATP).

The deblocking agent should be a strong nucleophilic agent which can hydrolyze the —C—S— bond and deblock the thiol moiety. It should not interfere with the conjugation reaction. For example, hydroxylamine does not react with either thiol or maleimide groups and, thus, will not interfere with the conjugation reaction. Hydroxylamine hydrochloride is the preferred deblocking agent. Cross-linking reagents which can functionalize a composition with a group that can react efficiently with free thiols, such as maleimide or pyridyl disulfide groups, or activated halogen groups can be used to practice the process of this invention. There can be mentioned N-succinimidyl-4-(N-maleimidomethyl)-cyclohexane-1-carboxylate (SMCC), N-maleimidobenzoyl-N-hydroxysuccinimide ester (MBS), and succinimidyl-4-(p-maleimidophenyl) butyrate (SMBP). Maleimides, pyridyl disulfide groups and activated halogen groups are the preferred thiol reactive groups.

The following illustrate reactions using these reactive groups:

Maleimide Reaction Scheme

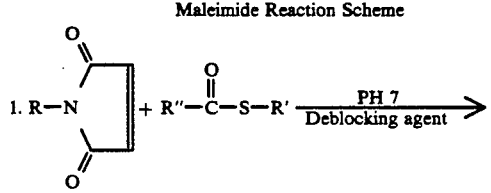

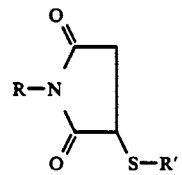

Pyridyl Disulfide Reaction Scheme

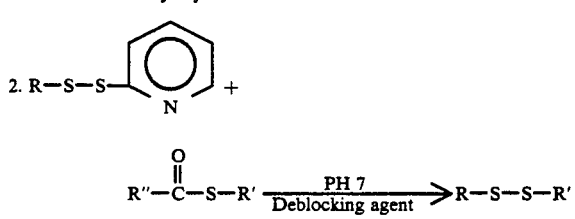

Active Halogen Reaction Scheme

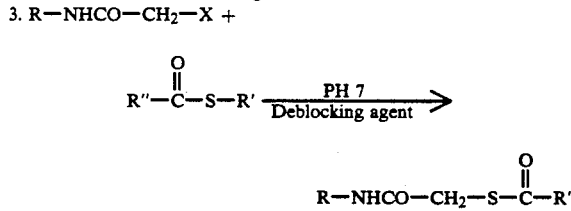

R: A protein, peptide, nucleotide, modified lipid, or any particle or solid support with derivatized amine groups on the surface.

R': A protein, peptide, nucleotide, modified lipid, or any particle or solid support with derivatized amine groups on the surface.

R'': A lower alkyl or phenyl group.

X: Halogen (Iodine, Bromine, chlorine, Fluorine).

Deblocking agent: A strong nucleophilic agent which can hydrolyze the —C—S— bond and deblock the thiol group.

The invention can be further understood by the following examples:

EXAMPLE 1

Preparation of an Antibody-Enzyme Conjugate

Preparation of Anti-TSH-(Fab')$_2$-Alkaline Phosphatase Conjugate

A. Functionalization of anti-TSH-(Fab')$_2$ with a Thiol Reactive Group

Anti-TSH-(Fab')$_2$ antibody fragments were prepared from an anti-TSH monoclonal IgG antibody obtained from the Hybritech hybridoma cell line identified as 972.2. IgG was isolated from ascites fluid derived from the cell line by affinity chromatography using a Protein-A-sepharose CL 4B column (Pharmacia Co.). IgG was eluted from the column with sodium acetate buffer, pH 3.0 and then dialyzed against 10 mM sodium phosphate and 300 mM sodium chloride solution, pH 7.0. The isolated IgG solution was then digested with a 50:1 molar ratio of pepsin at 37° C. for 65 minutes. Anti-TSH-(Fab')$_2$ antibody fragments were isolated from the resulting solution by affinity chromatography using a protein-Asepharose CL 4B column (Pharmacia Co.). The anti-TSH-(Fab')$_2$ antibody fragments were eluted from the column with 1M glycine, 1M sodium chloride, pH 8.6, and then purified by HPLC size exclusion column chromatography using a GF-250 XL column (Du Pont Co.). 1 mL of a solution containing 5 mg/mL anti-TSH-(Fab')$_2$ was dialyzed against 1000 volumes of 10 mM Na-phosphate/300 mM NaCl buffer, pH 7.0, and held overnight at 2°-8° C. with constant stirring. After dialysis, the (Fab')$_2$ containing solution was transferred into a dark vial. The antibody fragment solution was then treated with a 10 fold molar excess of the cross-linking reagent, N-succinimidyl-4-(N-maleimidomethyl)cyclo-hexane-1-carboxylate (SMCC) (Pierce Co.) in dimethyl sulfoxide (DMSO). The reaction mixture was allowed to rock gently at room temperature for 30 minutes. The mixture was then loaded onto a Sephadex G-25 column (1.0 cm×30 cm), and eluted with 10 mM Na-phosphate/300 mM NaCl buffer, pH 6.5. The fractions were collected and pooled to provide the maleimide-functionalized (Fab')$_2$ solution.

Figure 2A:
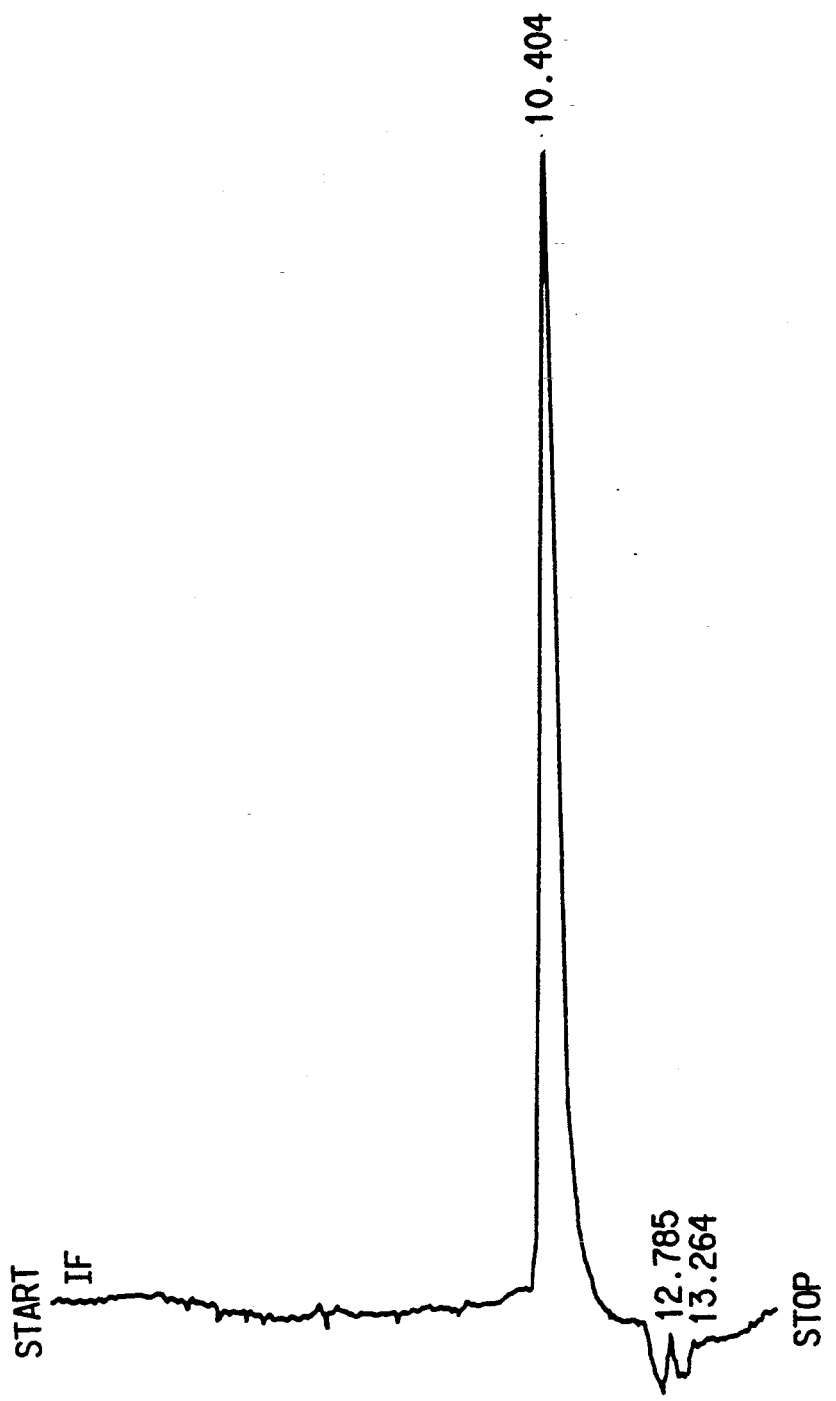
FIG. 2A presents the chromatogram for native alkaline phosphatase.

B. Functionalization of Alkaline Phosphatase 1 mL of a 10 mg/mL solution of alkaline phosphatase stock solution (Boehringer-Mannheim Biochemicals) was dialyzed against 1000 volumes of 10 mM Na-phosphate/300 mM NaCl buffer, pH 7.0, and held overnight at 2°-8° C. with constant stirring. After dialysis, the enzyme solution was transferred to a dark vial and the protein concentration adjusted by adding dialysis buffer to the solution. The final enzyme solution protein concentration was adjusted to 5 mg/mL. The enzyme solution was treated with a 15 fold molar excess of N-succinimidyl-S-acetylthioacetate (SATA) (Calbiochem.) in dimethyl sulfoxide (DMSO) to introduce blocked thiol groups. The reaction mixture was allowed to rock gently at room temperature for 30 minutes, loaded onto a Sephadex G-25 column (1.0×30 cm), and then eluted with 10 mM Na-phosphate/300 mM NaCl buffer, pH 6.5. The fractions were collected and pooled to provide acetylthiolated alkaline phosphatase. The chromatograms presented in FIG. 2 were obtained by separating about 10 μL of native and acetyl-thiolated alkaline phosphatase by HPLC on a GF-450 size exclusion column (9.4 cm×25 cm) (Du Pont Co.) and eluting in 0.2M Na-phosphate buffer, pH 7.0, at a flow rate of 1 mL/min. The effluent was monitored at 280 nm. Characteristic peaks of native alkaline phosphatase (A) and acetylthiolated alkaline phosphatase (AP-SATA) are indicated in FIG. 2.

Figure 3A:
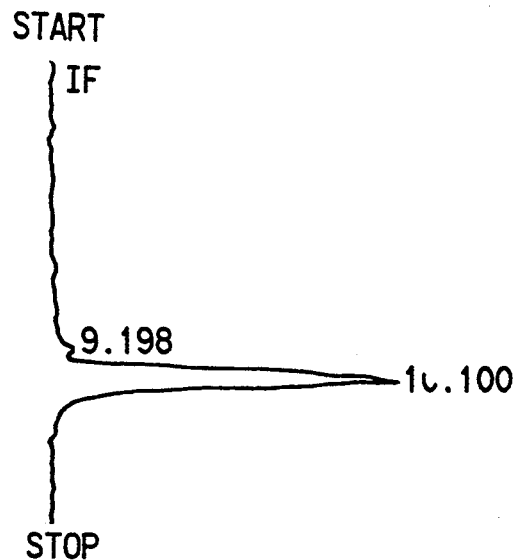
FIG. 3A presents the chromatograms of anti-TSH-(Fab')$_2$ functionalized with a thiol reactive group and acetylthiolated alkaline phosphatase at T=0 when $3 \times 10^{-5}$ mole/mL hydroxylamine deblocking agent was added.
Figure 3B:
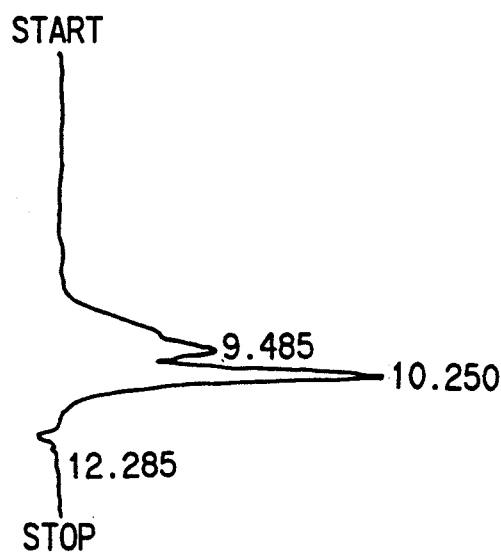
FIG. 3B presents the chromatograms of anti-TSH-(Fab')$_2$ functionalized with a thiol reactive group and acetylthiolated alkaline phosphatase at T=15 minutes when $3 \times 10^{-5}$ mole/mL hydroxylamine deblocking agent was added.
Figure 3C:
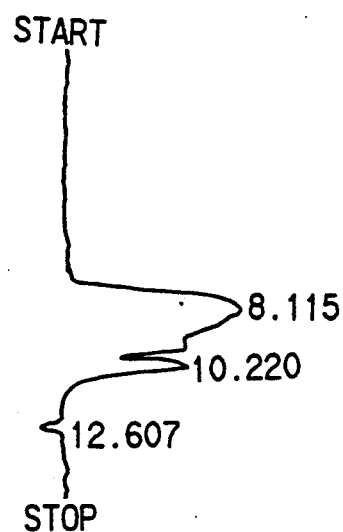
FIG. 3C presents the chromatograms of anti-TSH-(Fab')$_2$ functionalized with a thiol reactive group and acetylthiolated alkaline phosphatase at T=60 minutes when $3 \times 10^{-5}$ mole/mL hydroxylamine deblocking agent was added.

C. Deblocking and Conjugation 2.9 mL of a 1.10 mg/mL solution of maleimide-functionalized anti-TSH-(Fab')$_2$ was added to 4.1 mL of a 1 mg/mL solution of acetylthiolated alkaline phosphatase (AP) and treated with 210 μL of 1M hydroxylamine, pH 7.0. The reaction mixture was allowed to rock gently at room temperature for 60 minutes. The conjugation reaction was monitored by HPLC using a GF-450 size exclusion column (9.4 cm×25 cm) (Du Pont Co.) until the reaction was complete. The chromatograms presented in FIG. 3 were taken at (A) T=0 minute, (B) T=15 minutes, and (C) T=60 minutes. About 10 μL of the conjugate mixture was eluted in 0.2M Na-phosphate buffer, pH 7.0 at a flow rate of 1 mL/min. The effluent was monitored at 280 nm. These chromatograms indicate the characteristic peaks obtained for functionalized anti-TSH-(Fab')$_2$ and acetylthiolated alkaline phosphatase mixture when $3 \times 10^{-5}$ mole/mL hydroxylamine was added. FIG. 3(A) shows the absence of aggregation at the initial time point, T=0, just prior to the beginning of the conjugation reaction.

Conjugation reaction was quenched at room temperature by the addition of 7 μl of 0.1M N-ethylmaleimide (NEM) solution. After 30 minutes the crude conjugate solution was concentrated (using an Areicon stirred-cell, PM 30 membrane) to 2 mL.

D. Conjugate Separation

Figure 4:
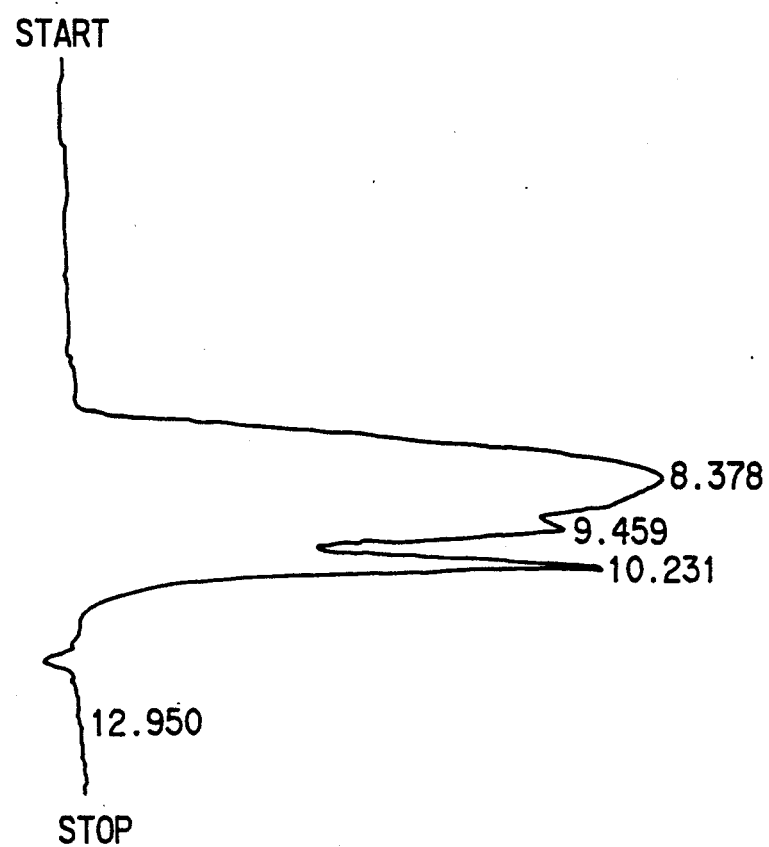

The anti-TSH-(Fab')$_2$-alkaline phosphatase conjugate was purified by HPLC using a GF-450 XL size exclusion column (22.5 mm×25 cm). The conjugate was eluted with 0.2M Na-phosphate buffer, pH 7.0 at a flow rate of 2 mL/min. The effluent was monitored at 280 nm. Two 1 mL injections were made and the fractions (1.0 ml each) were collected. Fractions having both immunoactivity and enzymatic activity were pooled. The results are shown in FIG. 4.

The conjugate peaks were clearly separated from the free enzyme or antibody fragment, (Fab')$_2$. The pooled conjugate was evaluated for immunoactivity in a 50% bound radioimmunoassay (RIA) using an $^{125}$I labeled antigen (TSH) (Du Pont) according to the procedures described in Dwenger, *J. Clin. Chem. Chin. Biochem.*, 22:883–894 (1984) and Yellow et al., *J. Clin. Invest.* 39:1157–1175 (1960). The results are presented in Table 1.

TABLE 1

| 50% Bound RIA For Anti-TSH-(Fab')$_2$ Immunoactivity | | |
|---|---|---|
| Sample | Concentration (mo/mL) | 50 % Titer per mg/mL |
| Anti-TSH-(Fab')$_2$ | 10 | $3.37 \times 10^4$ |
| Anti-TSH-(Fab')$_2$-maleimide | 1.01 | $3.38 \times 10^4$ |
| Anti-TSH-AP | 0.10 | $1.28 \times 10^4$ |
| Conjugate | 0.10 | $1.28 \times 10^4$ |

Using an RIA 50% titer, Table 1 shows that the conjugate immunoactivity appeared to be lower than that of the original antibody. However, the enzyme contributes at least half of the molecular weight and UV absorption in the conjugate complex. Thus, the immunoactivity indicated for the conjugate was due to about one-half of the amount of antibody present.

Anti-TSH-AP conjugate prepared by the in situ process was also evaluated in a TSH sandwich enzyme immunoassay. In the assay, TSH analyte (Du Pont) is first captured by chromium dioxide magnetic particles containing mouse monoclonal antibody specific to TSH. This monoclonal antibody was obtained from Du Pont hybridoma cell line 4/46.2 which was generated by immunizing BALB/c mice with pure whole TSH according to the process described by Freund, *J. Adv. Tuberc. Res.*, F:130-148 (1956). Spleen lymphocytes were obtained and fused with myeloma cells using standard techniques. Galfre et al., *Nature*, 266:550-552 (1976). The procedure of Engvall et al., *J. Immunol.*, 109:129-135 (1972) was used to screen the resulting clones. 25 μL samples of TSH analyte at 0 and 50 μI-U/ml were added to these antibody containing chromium dioxide particles and incubated at 37° C. for 30 minutes. The antibody was attached to the chromium dioxide magnetic particles using the method disclosed in U.S. Pat. No. 4,661,408. Next, 200 μL of the anti-TSH-AP conjugate (1.7 μg/mL) described above was added and incubated at 37° C. for 30 minutes. Excess anti-TSH-AP conjugate was then washed from the reaction chamber and the bound alkaline phosphatase was measured on a SLM Aminco fluorometer using a fluorometric substrate, methylumbelliferyl phosphate (MUP).

A comparison of the yield of conjugate obtained from the in Situ and non-in situ processes is shown in Table 2.

TABLE 2

Comparison of Yield for Anti-TSH-(Fab')₂-AP Conjugate In Situ Process and Non In Situ Process

| Process | Thiolating Reagent | Cross-linking Reagent | Yield (no. test/mg conjugate)* |
|---|---|---|---|
| In Situ | SATA/(Fab')₂ | SMCC/AP | 2612 |
| Non-In Situ | SATA/(Fab')₂ | SMCC/AP | 1627 |

*number of test assays possible per mg of conjugate; the improved yield obtained with the situ process of this invention based on the number of test assays possible per mg of conjugate prepared.

Alkaline phosphatase activity in the conjugate complex is shown in Table 3.

TABLE 3

| Alkaline Phosphatase Specific Activity | |
|---|---|
| Sample | Specific Activity (U/mg)* |
| AP | 1661 |
| AP-SATA | 1822 |
| Anti-TSH-AP conjugate | 730 |

*Alkaline phosphatase activity was measured in the Instrument Dimension ® (Du Pont Co.). Specific activity is defined by enzyme units, (U) per mg of enzyme protein where one unit is activity required to convert 1 μmole of substrate/minute at 37° C.

Table 3 shows the relative activity as measured for alkaline phosphatase, AP-SATA, and anti-TSH-AP conjugate. The conjugate alkaline phosphatase activity appears to be lower than that of the original enzyme. However, at least half of the molecular weight and UV absorption in the conjugate complex is contributed by the presence of the antibody so that the alkaline phosphatase activity indicated for the conjugate is due to about one-half of the amount of enzyme present.

EXAMPLE 2

Preparation of an Antibody-Receptor Protein Conjugate (Anti-HCG-IgG-Streptavidin Conjugate)

A. Functionalization of Streptavidin

Receptor proteins can also be used to prepare conjugates using the in situ process of this invention. Typically, preparation 5 mg of streptavidin (Bethesda Research Laboratories) was reconstituted with 0.65 mL of 10 mM Na-phosphate/300 mM NaCl/1 mM EDTA buffer, pH 7.0. The solution was treated with a 10 fold molar excess of N-Succinimidyl S-acetylthioacetate (SATA) in dimethyl sulfoxide (DMSO). The reaction mixture was allowed to rock gently at room temperature for 30 minutes and was then loaded on a Sephadex G-25 column (0.7 cm×30 cm) and eluted with 10 mM Na-phosphate/300 mM NaCl buffer, pH 6.5. The fractions were collected and pooled to provide the acetylthiolated streptavidin. Approximately 10 μL of native streptavidin (A) and acetylthiolated streptavidin (B) were separated by HPLC using a GF-250 size exclusion column (9.4 cm×25 cm) (Du Pont Co.) and eluted in 0.2M Na-phosphate buffer, pH 7.0, at a flow rate of 1 mL/min. The effluent was monitored at 280 nm.

Figure 5A:
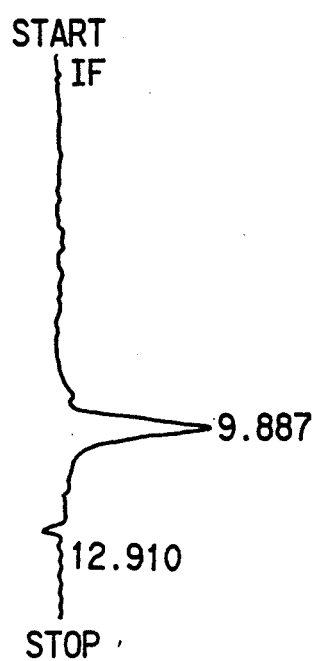
FIG. 5A presents the chromatogram for native streptavidin.
Figure 5B:
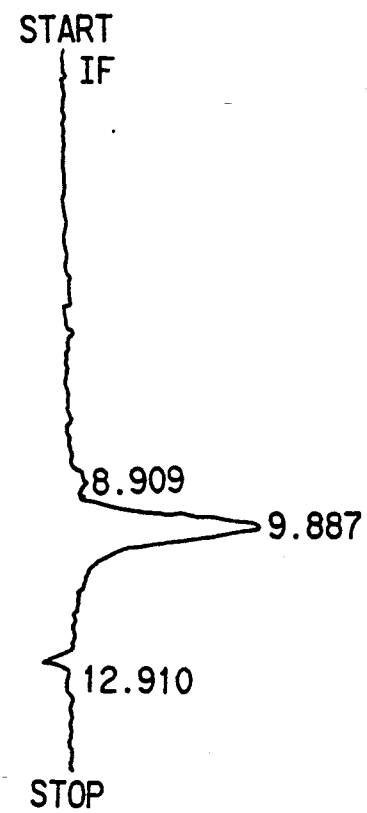
FIG. 5B presents the chromatogram for acetyl-thiolated streptavidin.

The chromatograms presented in FIG. 5 indicate the characteristic peaks obtained for native and acetylthiolated streptavidin.

B. Functionalization of Anti-HCG-IgG

Anti-HCG-IgG was prepared from IgG obtained from Du Pont hybridoma cell line 34/25.2 which was generated by immunizing BALB/c mice with pure whole HCG according to the process described by Freund, *J. Adv. Tuberc. Res.*, F:130-148 (1956). Spleen lymphocytes were obtained and fused with myeloma cells using standard techniques Galfre et al., *Nature*, 266:550-552 (1976). The procedure of Engvall et al., *J. Immunol.*, 109:129-135 (1972) was used to screen the resulting clones. 2.5 mL of 4.14 mg/mL anti-HCG-IgG was dialyzed against 1000 volumes of 10 mM Na-phosphate/300 mM NaCl buffer, pH 7.0 and held overnight at 2°-8° C. with constant stirring. After dialysis, the IgG solution was transferred to a dark vial. The solution was treated with a 10 fold molar excess of N-succinimidyl-4-(N-maleimidomethyl)-cyclohexane-1-carboxylate (SMCC) (Pierce), dissolved in dimethyl sulfoxide (DMSO). The reaction mixture was allowed to rock gently at room temperature for 30 minutes. Then the mixture was loaded onto a Sephadex G-25 column (1.0 cm×30 cm) and eluted with 10 mM Na-phosphate/300 mM NaCl buffer, pH 6.5. Fractions were collected and pooled to provide the maleimide-functionalized anti-HCG IgG.

C. Deblocking and Conjugation 4.09 mL of a 1.92 mg/mL solution of maleimide-functionalized anti-HCG-IgG was added to 1.89 mL of a 1.71 mg/mL solution of acetylthiolated streptavidin and treated with 180 μL of 1M hydroxylamine, pH 7.0. The reaction mixture was allowed to rock gently at room temperature for 60 minutes. The conjugation reaction was monitored by HPLC using a GF-250 size exclusion column (9.4 cm×25 cm) (Du Pont Co.) until the reaction was complete. About 10 μL of the conjugate mixture at (A) T=0 min., (B) T=15 min., and (C) T=60 min., were separated by HPLC using a GF-450 size exclusion column (9.4 cm×25 cm) (Du Pont Co.) and eluted in 0.2M Na-phosphate buffer, pH 7.0, at a flow rate of 1 mL/min. The effluent was monitored at 280 nm.

The chromatograms presented in FIG. 6 indicate the characteristic peaks obtained for the activated anti-HCG-(Fab')$_2$ and acetylthiolated streptavidin mixture using $3 \times 10^{-5}$ mole/mL hydroxylamine. FIG. 6 shows the absence of aggregation at the initial time point, T=0, just prior to the beginning of the conjugation reaction. Furthermore, FIG. 6 shows that the conjugation reaction was quenched at room temperature by the addition of 6 μL of 0.1M of mercaptoethylamine solution. After 30 minutes the crude conjugate solution was concentrated (using an Amicon stirred-cell, PM 30 membrane) to 2 mL.

D. Conjugate Separation

The crude anti-HCG-IgG-streptavidin conjugate was purified by HPLC using a GF 250 XL size exclusion column (22.5 mm×25 cm) (Du Pont Co.). The conjugate was eluted with 0.2M Na-phosphate buffer, pH 7.0 at a flow rate of 2 ml/minute. Two 1 mL injections were made and two 1.0 mL fractions (1.0 mL each) were collected. Fractions that had both immunoactivity and streptavidin binding activity were pooled. The effluent was monitored at 280 nm.

Figure 7:
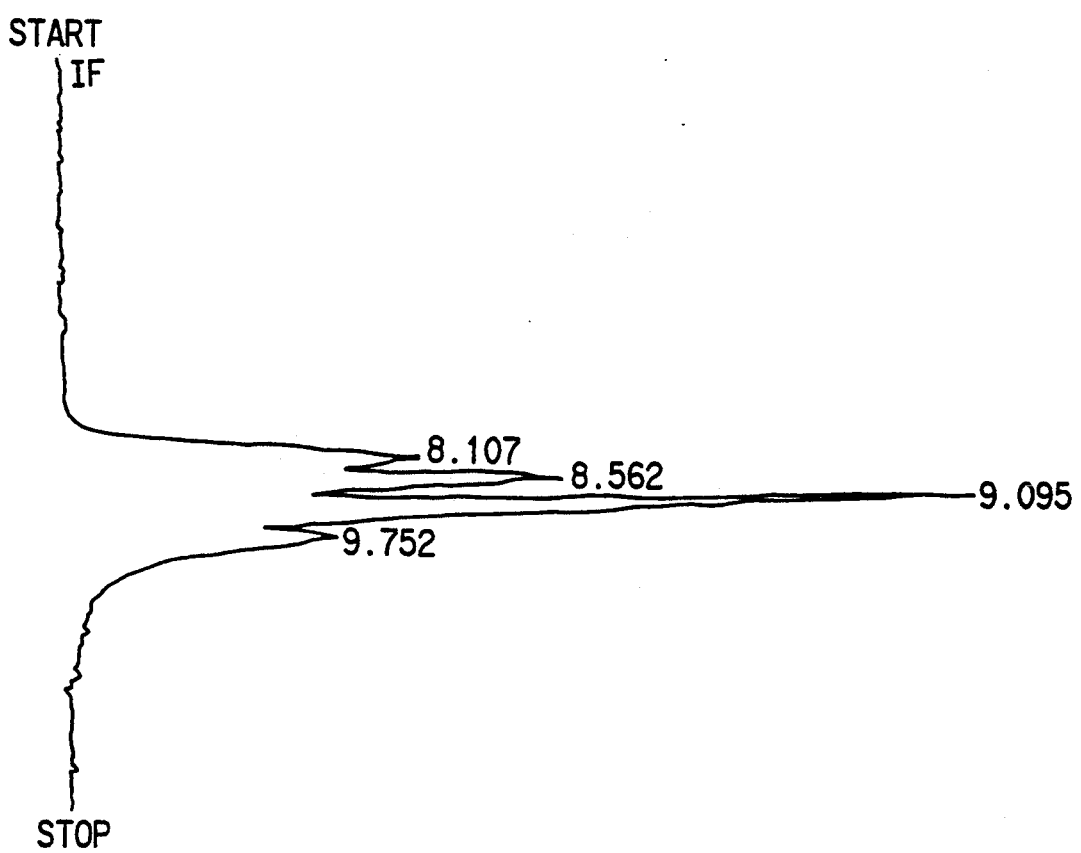
FIG. 7 is a chromatogram of anti-HCG-IgG-streptavidin conjugate.

The results in FIG. 7 show that the first 2 peaks were anti-HCG-IgG-streptavidin conjugates. The third peak was anti-HCG-IgG and the fourth peak was streptavidin. The pooled conjugate was evaluated in a 50% bound RIA test as described above using I$^{125}$ labeled HCG (Du Pont Co.) as antigen for the anti-HCG-IgG immunoactivity according the procedures described above. The results are shown in Table 4.

TABLE 4

| 50% Bound RIA For Ani-HCG-IgG Immunoactivity | | |
|---|---|---|
| Sample | Concentration (mg/mL) | 50% Titer per mg/mL |
| Anti-HCG-IgG | 4.1 | $2.76 \times 10^4$ |
| Anti-HCG-IgG-maleimide | 0.1 | $1.91 \times 10^4$ |
| Anti-HCG-ST.AV* conjugate | 0.237 | $8.34 \times 10^3$ |

*ST.AV is defined as Streptavidin

Table 4 shows the relative immunoactivity as measured for anti-HCG-IgG, anti-HCG-IgG-maleimide, and anti-HCG-ST.AV conjugate. The conjugate anti-HCG-ST.AV immunoactivity appears to be lower than that of the original IgG. However, the apparent specific activity of the conjugate is reduced due to the presence of streptavidin in the conjugate complex. The streptavidin binding activity was evaluated by the HABA test as described by Green, N. M., *Biochem. J.*, 94:23C (1965). Binding of the dye, 4-hydroxyazobenzene-2'-carboxylic acid (HABA), by streptavidin was accompanied by spectral changes due to absorption in the range of 350 nm to 500 nm. The results are shown in Table 5.

TABLE 5

| Binding of HABA to streptavidin and Streptavidin-anti-HCG-IgG conjugate | | |
|---|---|---|
| Sample | Streptavidin (mole/assay) | HABA mole/ assay | Absorbance at 500 nm (Absorbance) |
| Streptavidin | $9.5 \times 10^{-9}$ | $2.5 \times 10^{-7}$ | 0.76 |
| Streptavidin | $4.75 \times 10^{-9}$ | $1.25 \times 10^{-7}$ | 0.32 |
| Streptavidin | $2.37 \times 10^{-9}$ | $6.25 \times 10^{-8}$ | 0.096 |
| Streptavidih | $1.18 \times 10^{-9}$ | $3.12 \times 10^{-8}$ | 0.038 |

TABLE 5-continued

| Binding of HABA to streptavidin and Streptavidin-anti-HCG-IgG conjugate | | |
|---|---|---|
| Sample | Streptavidin (mole/assay) | HABA mole/ assay | Absorbance at 500 nm (Absorbance) |
| Anti-HCG-ST.AV* conjugate | $1.07 \times 10^{-9}$ | $3.12 \times 10^{-8}$ | 0.035 |

*Anti-HCG-IgG-ST.AV conjugate concentration by estimation based on 1/1 molar ratio of streptavidin/IgG with an extinction coefficient at 280 nm = 1.8 for a 0.1% conjugate solution.

Table 5 demonstrates that the anti-HCG-streptavidin conjugate exhibited about the same binding activity as streptavidin where the conjugate contained an equal amount of streptavidin.

EXAMPLE 3

Using Fluorescein As An Internal Label To Demonstrate Absence of Self-Conjugation In The Preparation Of Anti-HCG-(Fab')$_2$-Alkaline Phosphatase Conjugate

A. Functionalization And Fluorescein Labeling Of Anti-HCG-(Fab')$_2$

Anti-HCG-(Fab')$_2$ fragments were prepared from IgG obtained from the Hybritech cell line identified as 514.2 according to the procedure described above in Example 1. 1.13 mL of 4.27 mg/mL anti-HCG-(Fab')$_2$ solution was dialyzed against 1000 volumes of 10 mM Na-phosphate/300 mM NaCl buffer, pH 7.0 and held overnight at 2°-8° C. with constant stirring. After dialysis, the (Fab')$_2$ solution was transferred into a dark vial. The solution was treated with a 15 fold molar excess of N-succinimidyl-4-(N-maleimidomethyl-cyclohexane-1-carboxylate (SMCC) (Pierce Co.), in 24 μL of dimethyl sulfoxide (DMSO). The reaction mixture was allowed to rock gently at room temperature for 30 minutes. The functionalized anti-HCG-(Fab')$_2$ solution was then treated with a 15 fold molar excess of fluorescein-5-isothiocyanate (FITC) (Molecular Probes Co.) in dimethyl sulfoxide (DMSO). The mixture was allowed to continue to react for another 30 minutes. The mixture was then loaded onto a Sephadex G-25 column (1.0 cm×30 cm) and eluted with 10 mM Na-phosphate/300 mM NaCl buffer, pH 6.5. Fractions were collected and pooled to provide the fluorescein labeled and maleimide-functionalized (Fab')$_2$.

B. Functionalization Of Alkaline Phosphatase 1 mL of a 10 mg/mL alkaline phosphatase stock solution (Boehringer Mannheim Biochemicals) was dialyzed against 1000 volumes of 10 mM Na-phosphate/300 mM NaCl buffer, pH 7.0, and held overnight at 2°-8° C. with constant stirring. After dialysis, the enzyme solution was transferred to a dark vial and the protein concentration was adjusted by adding dialysis buffer to the solution. The final enzyme solution protein concentration was adjusted to 5 mg/mL. The enzyme solution was treated with a 15 fold molar excess of N-Succinimidyl-S-acetylthioacetate (SATA) in dimethyl sulfoxide (DMSO). The reaction mixture was allowed to rock gently at room temperature for 30 minutes and was then loaded onto a Sephadex G-25 column (1.0 cm×30 cm) and eluted with 10 mM Na-phosphate/300 mM NaCl buffer, pH 6.5. The fractions were collected and pooled to provide acetylthiolated alkaline phosphatase.

Figure 8A:
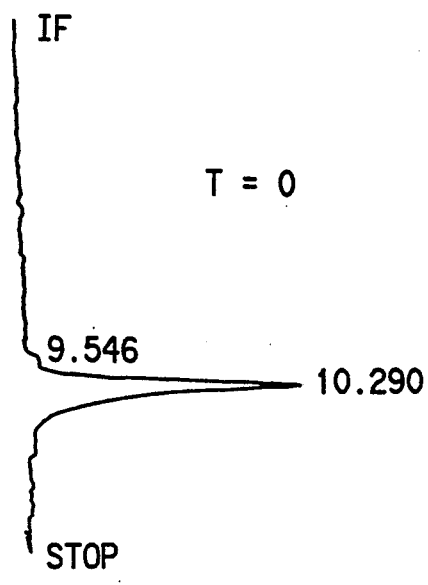
FIG. 8A presents the chromatogram of anti-HCG-(Fab')$_2$-fluorescein functionalized with a thiol reactive group and acetylthiolated alkaline phosphatase at T=0 minutes when $3 \times 10^{-5}$ mole/mL hydroxylamine deblocking agent was added.
Figure 8B:
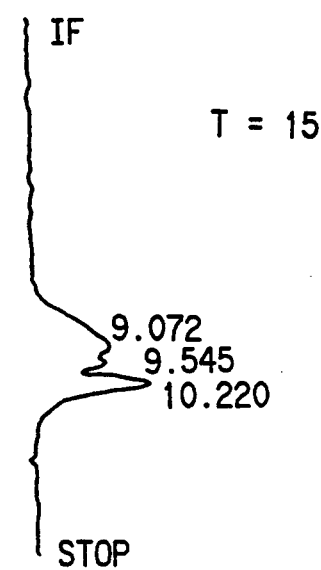
FIG. 8B (like 8A except T=15 minutes).
Figure 8C:
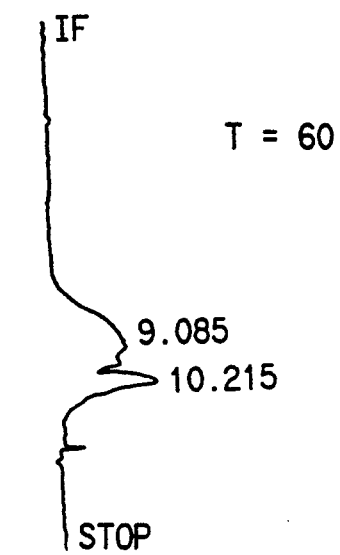
FIG. 8C (like 8A except T=60 minutes).

C. Deblocking and Conjugation 2.81 mL of a 1.185 mg/mL solution of maleimide-functionalized anti-HCG-(Fab')$_2$-*F solution was added to the solution of acetylthiolated alkaline phosphatase and was then treated with 115 μL of 1M hydroxylamine, pH 7.0. The reaction mixture was allowed to rock gently at room temperature for 60 minutes. The conjugation reaction was monitored by HPLC using a GF-450 column (Du Pont Co.) until the reaction was complete. The chromatograms obtained are shown in FIG. 8. About 10 μL of the conjugate mixture at (A) T=0 min., (B) T=15 min., and (C) T=60 min., were separated by HPLC using a GF-450 size exclusion column (9.4 cm×25 cm) (Du Pont Co.) and eluted in 0.2M Na-phosphate buffer, pH 7.0, at a flow rate of 1 mL/min. The effluent was monitored at 280 nm.

FIG. 8 indicates the characteristic peaks obtained for the functionalized anti-HCG-(Fab')$_2$-*F and acetylthiolated alkaline phosphatase mixture with $3 \times 10^{-5}$ mole/mL hydroxylamine.

The crude conjugate solution was concentrated (using an Amicon stirred-cell, PM 30 membrane) to 2 mL.

D. Conjugate Separation

Figure 9:
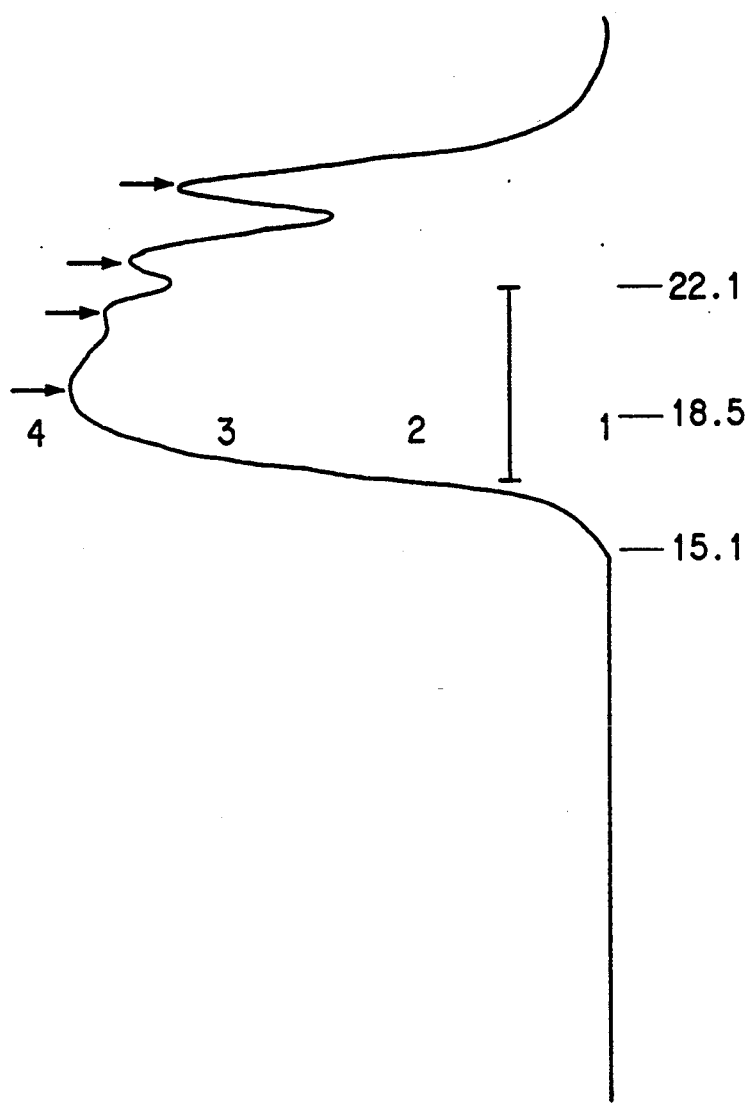
FIG. 9 is a chromatogram of anti-HCG-(Fab')$_2$-*F-AP conjugate.

The anti-HCG-(Fab')$_2$-*F-alkaline phosphatase conjugate was purified by HPLC using a GF 450 XL column. The conjugate was eluted with 0.2M Na-phosphate buffer, pH 7.0. Two of the 1 mL injections were made and two fractions (1.0 mL each) were collected. Fractions that had immunoactivity, fluorescent emission, and enzymatic activity were pooled. The chromatogram for one of the injections is shown in FIG. 9. 1 mL of crude anti-HCG-(Fab)$_2$-*F-AP conjugate was separated by HPLC using a GF-450 XL size exclusion column (22.5 mm×25 cm) (Du Pont Co.) and eluted in 0.2M Na-phosphate buffer, pH 7.0, at a flow rate of 2 mL/min. The effluent was monitored at 280 nm.

Figure 10A:
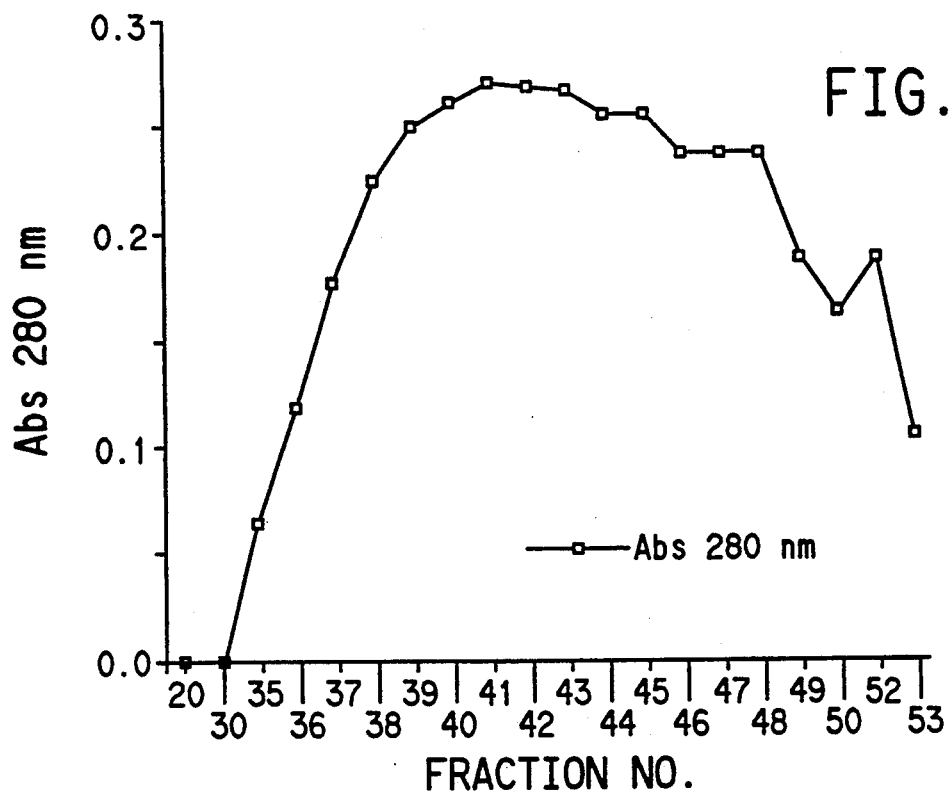
FIG. 10A is a chromatogram of anti-HCG-(Fab')$_2$*F-AP conjugate obtained with a UV monitor.
Figure 10B:
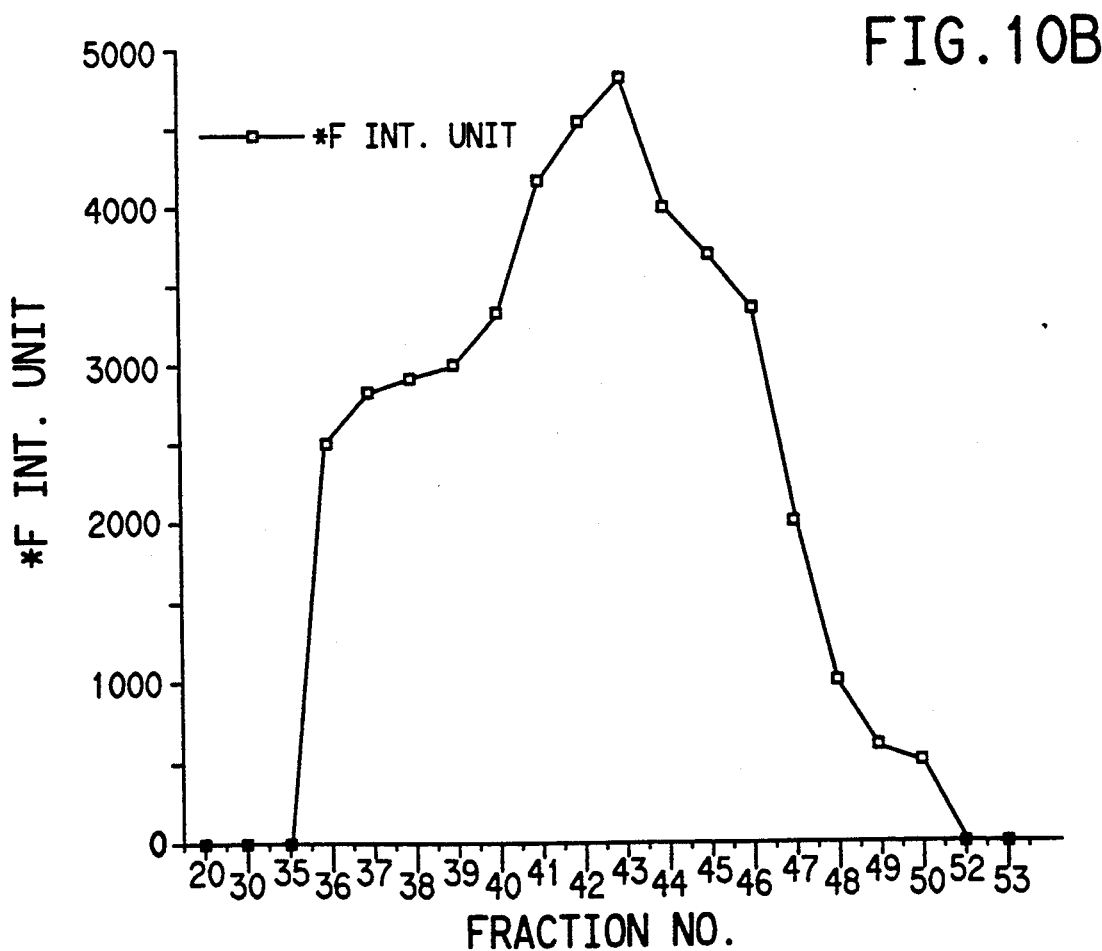
FIG. 10B is a chromatogram of anti-HCG-(Fab')$_2$*F-AP conjugate obtained with a fluorescent monitor.

As FIG. 9 indicates, the conjugate peaks were clearly separated from the free enzyme or antibody fragment, (Fab')$_2$. Each one of the conjugate fractions was also evaluated using an SLM Aminco photon counter 8000-C instrument. Each fraction was also read using a HP spectrophotometer 8452A at 280 nm absorption. The results are shown in FIG. 10.

These chromatograms show that all the conjugate fragments had fluorescent emission which correlated with the UV absorption fragments at 280 nm. This indicated there was no self conjugation of alkaline phosphatase to alkaline phosphatase. Each conjugate fragment had fluorescent (which had fluorescein labeled on (Fab')$_2$) activity. The pooled conjugate was evaluated in 50% bound radioimmunoassay according to the protocol described above using $^{125}$I labeled antigen (HCG) (Du Pont Co.). The results are shown in Table 6.

TABLE 6

50% Bound RIA For Anti-HCG-(Fab')$_2$ Immunoactivity

| | Concentration (mg/mL) | 50 % Titer |
|---|---|---|
| Anti-HCG-(Fab')$_2$ | 3.58 | $9.33 \times 10^4$ |
| Anti-HCG-(Fab')$_2$-*F maleimide | 0.237 | $4.388 \times 10^4$ |
| Anti-HCG-*F-AP crude conjugate | 0.18 | $2.42 \times 10^4$ |
| Anti-HCG-*F-AP conjugate | 0.071 | $2.08 \times 10^4$ |

*F = fluorescein label

Table 6 shows the relative immunoactivity as measured for anti-HCG-(Fab')$_2$, anti-HCG-(Fab')$_2$-*F-maleimide, anti-HCG-*F-AP crude conjugate, and anti-HCG-*F-AP conjugate. The conjugate immunoactivity appeared to be lower than that of the original IgG. However, the apparent specific activity of the conjugate is reduced due to the presence of streptavidin in the conjugate complex.

What is claimed is:

1. A process for conjugating two compounds which comprises mixing simultaneously (i) a first compound functionalized with a maleimide, (ii) a second compound containing blocked thiols, and (iii) a deblocking reagent wherein said deblocking reagent is hydroxylamine to generate free thiol groups wherein said simultaneous mixing is such that deblocking of the thiol and conjugation to the maleimide functionalized compound occurs substantially simultaneously and further wherein the first and second compounds can be the same or different and are selected from the group consisting of proteins, peptides, nucleotides and lipids derivatives with at least one amine group.

2. A process according to claim 1 wherein the first compound is functionalized with a heterobifunctional cross linking agent selected from the group consisting of SMCC, SMBP, and MBs and the second compound is functionalized with a thiolating reagent selected from the group consisting of SATP, SATA, and SAMSA.

* * * * *